United States Patent
Cha et al.

(10) Patent No.: US 11,730,416 B2
(45) Date of Patent: Aug. 22, 2023

(54) METHOD OF PROCESSING ELECTROCARDIOGRAM SIGNAL

(71) Applicant: ATSENS CO., LTD., Gyeonggi-do (KR)

(72) Inventors: Kab Mun Cha, Seoul (KR); Jong Ook Jeong, Gyeonggi-do (KR)

(73) Assignee: ATSENS CO., LTD., Gyeonggi-do (KR)

(*) Notice: Subject to any disclaimer, the term of this patent is extended or adjusted under 35 U.S.C. 154(b) by 192 days.

(21) Appl. No.: 17/177,726

(22) Filed: Feb. 17, 2021

(65) Prior Publication Data

US 2021/0251550 A1     Aug. 19, 2021

(30) Foreign Application Priority Data

Feb. 18, 2020    (KR) .......................... 10-2020-0019631

(51) Int. Cl.
     *A61B 5/352*     (2021.01)
     *A61B 5/0245*     (2006.01)
     *A61B 5/024*     (2006.01)
     *A61B 5/333*     (2021.01)
     *A61B 5/00*     (2006.01)
     *A61B 5/366*     (2021.01)

(52) U.S. Cl.
CPC ............ *A61B 5/352* (2021.01); *A61B 5/0006* (2013.01); *A61B 5/0245* (2013.01); *A61B 5/02405* (2013.01); *A61B 5/333* (2021.01); *A61B 5/366* (2021.01); *A61B 5/7203* (2013.01); *A61B 5/7221* (2013.01); *A61B 5/7267* (2013.01)

(58) Field of Classification Search
CPC . A61B 5/0006; A61B 5/02405; A61B 5/0245; A61B 5/333; A61B 5/352; A61B 5/366; A61B 5/7203; A61B 5/7221; A61B 5/7267; G16H 50/20
See application file for complete search history.

(56) References Cited

U.S. PATENT DOCUMENTS

| 2018/0125385 A1* | 5/2018 | Chauhan | A61B 5/366 |
| 2019/0082988 A1* | 3/2019 | Datta | A61B 5/316 |
| 2022/0022799 A1* | 1/2022 | Rapin | A61B 5/7264 |

FOREIGN PATENT DOCUMENTS

CN         105433917 A   *   3/2016

OTHER PUBLICATIONS

Sadhukhan, et al., R-peak Detection Algorithm for ECG Using Double Difference and RR Interval Processing, Procedia Technology, pp. 873-877, vol. 4, 2012, Elsevier Ltd.

* cited by examiner

*Primary Examiner* — Son T Le
*Assistant Examiner* — Adam S Clarke
(74) *Attorney, Agent, or Firm* — Guntin & Gust, PLC; Miyoung Shin

(57) ABSTRACT

A processing method using an electrocardiogram signal includes (a) selecting a candidate for an abnormal R-peak from the electrocardiogram signal, (b) determining an abnormal R-peak from among the candidates selected in (a), and (c) excluding the abnormal R-peak determined in (b) among all the R-peaks from the electrocardiogram signal.

9 Claims, 17 Drawing Sheets

Delete abnormal peaks

METHOD OF PROCESSING ELECTROCARDIOGRAM SIGNAL

CROSS-REFERENCE TO RELATED APPLICATION

This application is based on and claims priority under 35 U.S.C. § 119 to Korean Patent Application No. 10-2020-0019631, filed on Feb. 18, 2020, in the Korean Intellectual Property Office, the disclosure of which is incorporated by reference herein in its entirety.

BACKGROUND

1. Field

The present disclosure relates to a method of processing an electrocardiogram signal.

2. Related Art

Various algorithms may be searched for by using a method of detecting an R-peak of an electrocardiogram signal through Google (www.google.com).

However, the detected R-peak may not be accurate due to noise of an electrocardiogram signal. When an RR interval, which is a time interval between successive R-peaks, is calculated by using the R-peaks detected inaccurately as such, the RR interval is also inaccurate.

In addition, when a person manually detects an R-peak of an electrocardiogram signal and calculates an RR interval, the amount of manual detection and calculation may be limited, and thus, it is desirable to automate the method.

Procedia Technology 4, 2012, pages 873 to 877 (R-peak detection algorithm for ECG using double difference and RR interval processing, hereinafter, referred to as a technology of the related art) discloses a method of detecting an R-peak of an electrocardiogram signal and a method of calculating an RR interval which is an interval between the successive R-peaks by using the detected R-peak.

In the related art, in order to remove an incorrect R-peak while automatically calculating the RR interval, R-peaks are compared by using an average RR interval between five consecutive R peaks. When the RR interval is abnormal, a second R-peak is removed to calculate the RR interval, thereby calculating a correct RR interval.

However, in a case in which R-peaks are simply compared by using an average RR interval and the RR interval is calculated by removing a second R-peak when the RR interval is abnormal, there is a question as to whether or not only an abnormal R-peak is detected.

SUMMARY

The present disclosure provides a method of processing an electrocardiogram signal which is capable of accurately determining an abnormal electrocardiogram signal by determining whether or not the electrocardiogram signal is abnormal through two steps, as a disclosure for solving the technical problems described above.

Additional aspects will be set forth in part in the description which follows and, in part, will be apparent from the description, or may be learned by practice of the presented embodiments of the disclosure.

In one or more embodiments according to the present disclosure, a processing method using an electrocardiogram signal includes (a) selecting a candidate for an abnormal R-peak from the electrocardiogram signal, (b) determining an abnormal R-peak from among the candidates selected in (a), and (c) excluding the abnormal R-peak determined in (b) among all the R-peaks from the electrocardiogram signal.

Specifically, (a) described above may use at least one of an interval between the R-peaks of the electrocardiogram signal, and complexity of the electrocardiogram signal. When the interval between the R-peaks of the electrocardiogram signal is used, (a) described above includes (a-1-1) calculating the interval between the R-peaks of the electrocardiogram signal, and (a-1-2) selecting a corresponding R-peak as a candidate for an abnormal R-peak when the interval between the R-peaks calculated in (a-1-1) is less than a preset value. In addition, when using complexity of an electrocardiogram signal, (a) described above may include (a-2-1) calculating the complexity of a signal to a preset window size, and (a-2-2) selecting an R-peak included in a window in which the complexity of the signal calculated in (a-2-1) is out of a preset range as a candidate for an abnormal R-peak.

In addition, (b) described above desirably determine an abnormal R-peak from among candidates selected in (a) by comparing a waveform of an electrocardiogram signal during a preset time period based on a time representing the R-peak selected in (a) with a waveform of an electrocardiogram signal representing a normal R-peak. Here, the waveform of the electrocardiogram signal representing the normal R-peak is calculated by an average value of waveforms of the electrocardiogram signal for multiple R-peaks during a preset time period.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
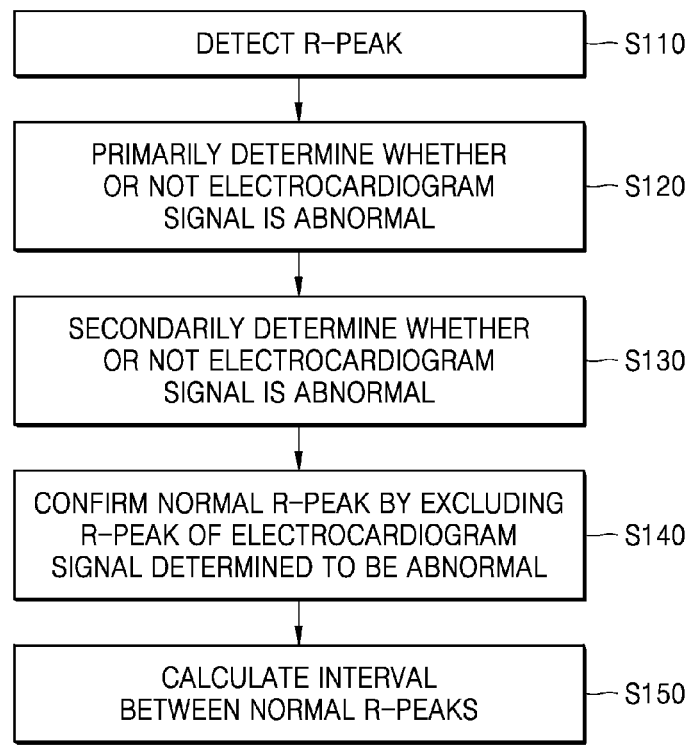
FIG. 1 is a flowchart illustrating a method of processing an electrocardiogram signal, according to one or more embodiments of the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, configurations and operations of the present disclosure will be described in detail with reference to embodiments of the present disclosure illustrated in the accompanying drawings.

The present disclosure may be variously changed and have various embodiments, and thus, various embodiments will be illustrated in the drawings and described in detail in the detailed description. Effects and characteristics of the present disclosure, and a method of achieving the effects and characteristics will be apparent with reference to the embodiments to be described below in detail together with the drawings. However, the present disclosure is not limited to the embodiments to be disclosed below and may be implemented in various forms.

Hereinafter, embodiments of the present disclosure will be described in detail with reference to the accompanying drawings, and when describing with reference to the drawings, the same or corresponding components are denoted by the same reference numerals, and redundant descriptions thereof will not be repeated.

In this specification, terms such as "learning" are not intended to refer to mental actions such as human educational activities but are intended to refer to performing machine learning through computational procedures.

In the following embodiments, terms such as "first" and "second" are not used in a limiting meaning but for the purpose of distinguishing one component from another component.

In the following examples, singular expressions include plural expressions unless the context clearly indicates otherwise.

In the following embodiments, a term such as "include" or "have" means that there are characteristics or components described in the specification, and do not preclude a possibility of adding one or more other characteristics or components.

In the drawings, components may be exaggerated or reduced in size for the sake of convenient description. For example, the size and thickness of each component illustrated in the drawings are randomly illustrated for the sake of convenient description, and thus the present disclosure is not limited to the illustration.

When a certain embodiment is implemented differently, a certain process order may also be performed differently from the described order. For example, two processes described in succession may also be performed substantially simultaneously or may be performed in an order opposite to the described order.

A method of processing an electrocardiogram signal according to one or more embodiments of the present disclosure may be implemented in the form of a computer program to be processed by a processor of a computing device.

FIG. 1 is a flowchart illustrating a method of processing an electrocardiogram signal, according to one or more embodiments of the present disclosure.

As can be seen from FIG. 1, a method of processing an electrocardiogram signal, according to an embodiment of the present disclosure, includes an R-peak detection step S110 of detecting an R-peak of an electrocardiogram signal by using an electrocardiogram signal processing device, a first determination step S120 of primarily determining whether or not an electrocardiogram signal is abnormal by using the electrocardiogram signal processing device, a second determination step S130 of secondarily determining whether or not the electrocardiogram signal is abnormal based on a result of the first determination step S120 by using the electrocardiogram signal processing device, a confirmation step S140 of confirming a normal R-peak by excluding an R-peak of the electrocardiogram signal determined to be abnormal in the second determination step S130 by using the electrocardiogram signal processing device, and a step S150 of calculating an interval between the normal R-peaks confirmed in the confirmation step S140.

In some forms, a method of processing an electrocardiogram signal may be performed by an electrocardiogram signal processing device. The electrocardiogram signal processing device may be implemented with hardware or software. The electrocardiogram signal processing device may be a computing device including one or more processors and may perform the method of processing an electrocardiogram signal by using the one or more processors. The electrocardiogram signal processing device may further include a memory. The memory may be electrically connected to the electrocardiogram signal processing device or may be connected to the electrocardiogram signal processing device through a network.

Here, the electrocardiogram signal may include one or more waveforms. For reference, the method of processing an electrocardiogram signal, according to one or more embodiments of the present disclosure, is performed on a preset detection region. In addition, the electrocardiogram signal used in the embodiments of the present disclosure is also referred to as a QRS signal.

Various known techniques of the related art including techniques of the related art described in the "Related Art" may be used as the method of detecting an R-peak in the R-peak detection step S110, and thus, a separate description will not be made.

In some forms, the first determination step S120 may be implemented by using two methods. One is a method of using a time interval between successive R-peaks of an electrocardiogram signal, and the other is a method of using the complexity of the electrocardiogram signal.

The two methods may also be used in the first determination step S120 or may also be used in the first determination step S120 by being combined with each other. For reference, as an example of a combination of the two methods, when an electrocardiogram signal is determined to be an abnormal electrocardiogram signal by at least one of the two methods, it is determined that the electrocardiogram signal is abnormal or in an abnormal period in the first determination step S120.

Figure 2A:
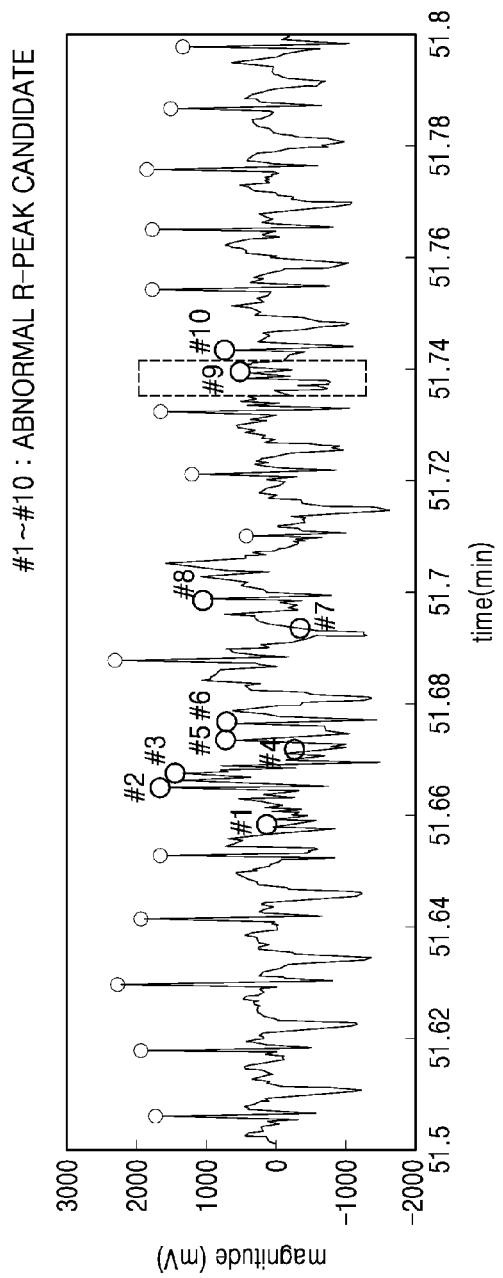
FIG. 2A is a graph provided by extracting an R-peak from an electrocardiogram signal.
Figure 2B:
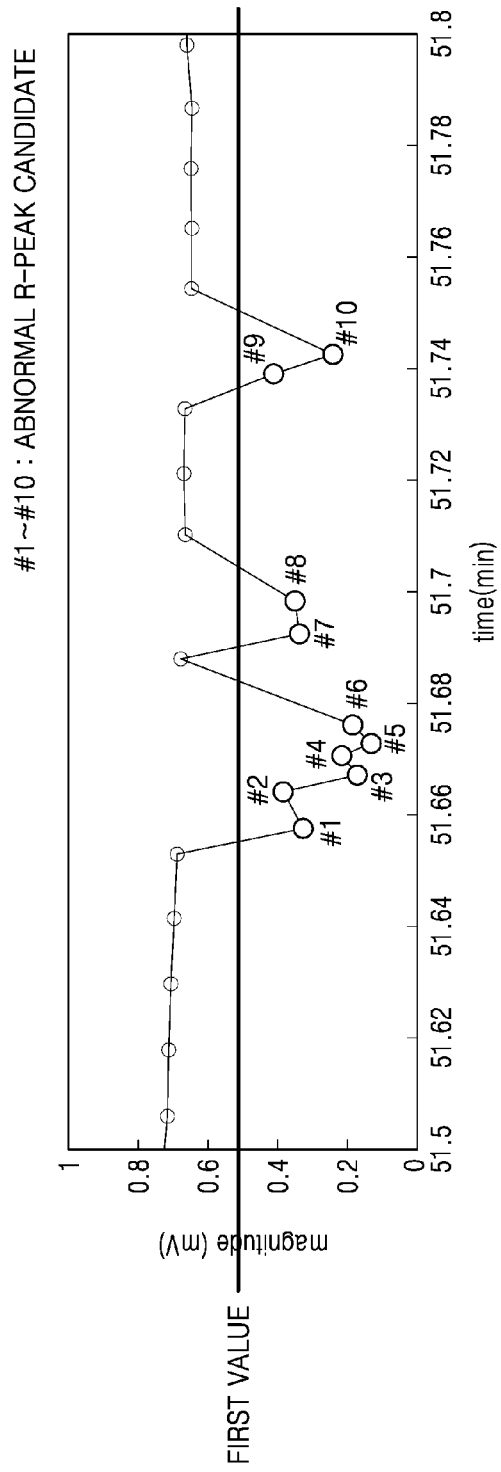
FIG. 2B is an exemplary diagram of an abnormal R-peak in an electrocardiogram signal.

FIG. 2A and FIG. 2B are flowcharts of the first determination step S120 using a time interval between a first R-peak and a second R-peak of an electrocardiogram signal.

The second R-peak may be referred to as a peak temporally adjacent to the first R-peak.

As illustrated in FIG. 2B, in a case in which an interval between the first R-peak and the second R-peak of the electrocardiogram signal is used, when the time interval (RR Interval) between the first R-peak and the second R-peak is less than a first value previously determined, the first R-peak may be primarily determined to be an abnormal R-peak in the first determination step S120. For reference, the R-peak determined as an abnormal R-peak becomes an R-peak that follows in time among the first R-peak and the second R-peak.

As illustrated in FIG. 2A, the first value may be set by using an average value of normal R-peaks of a normal electrocardiogram signal previously measured. For example, the first value may be set to 70% of the average value of the normal R-peaks.

Figure 3A:
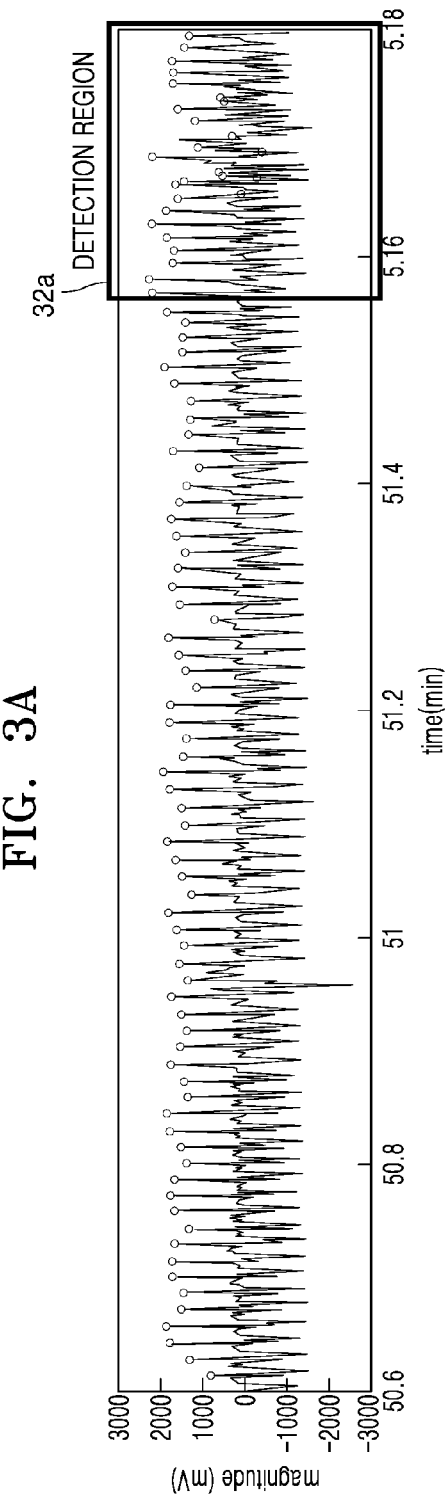
FIG. 3A is an exemplary diagram of a detection region in an electrocardiogram signal.
Figure 3B:
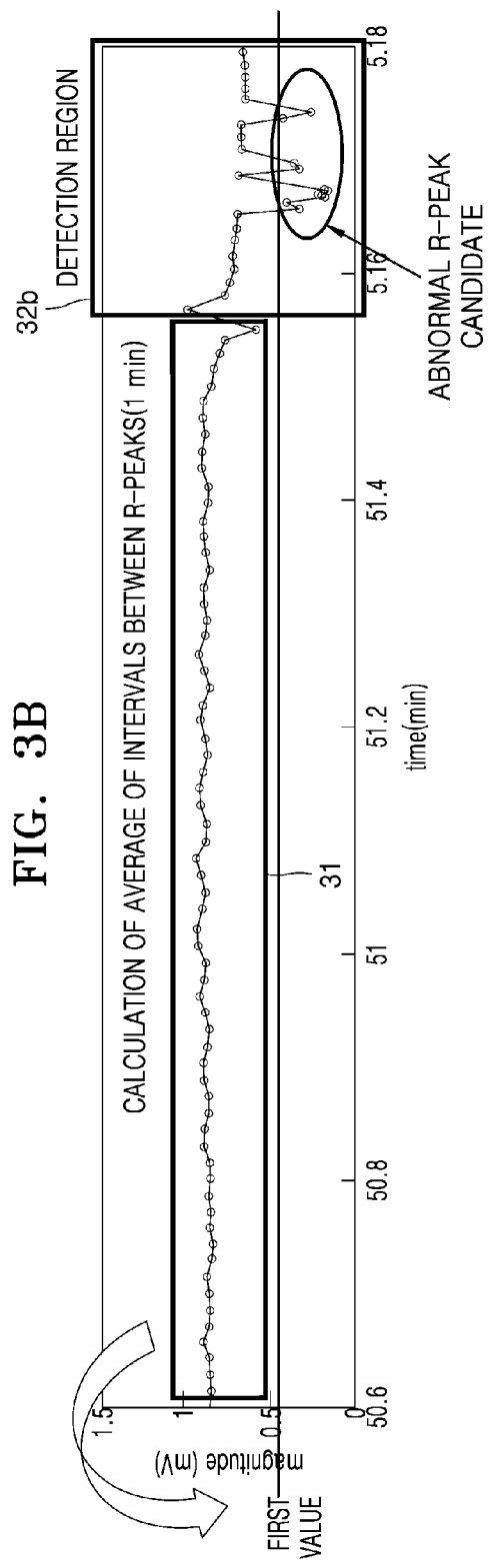
FIG. 3B is an exemplary diagram of an abnormal peak in a detection region in an electrocardiogram signal.

FIG. 3A and FIG. 3B are plots illustrating a process of determining an abnormal R-peak candidate.

As illustrated in FIG. 3A, the electrocardiogram signal processing device may designate a detection area for a part of the signal.

As illustrated in FIG. 3B, the electrocardiogram signal processing device may set the first value by using an average value of time intervals between normal R-peaks for a region 31 of the normal electrocardiogram signal. The electrocardiogram signal processing device may determine a candidate group of abnormal R-peaks by applying the first value to a detection region 32a, 32b. Here, a normal electrocardiogram signal may be an electrocardiogram signal except for waveforms determined as an abnormal period (cycle or interval) in the electrocardiogram signal. Determination of an abnormal period may be performed by a disclosed method of the present disclosure but may be determined by various methods without being limited thereto. Here, the detection region may refer to all or part of the electrocardiogram signal and may refer to a region determined by a user. The first value refers to a value that is a criterion for determining an abnormal R-peak.

Figure 4A:
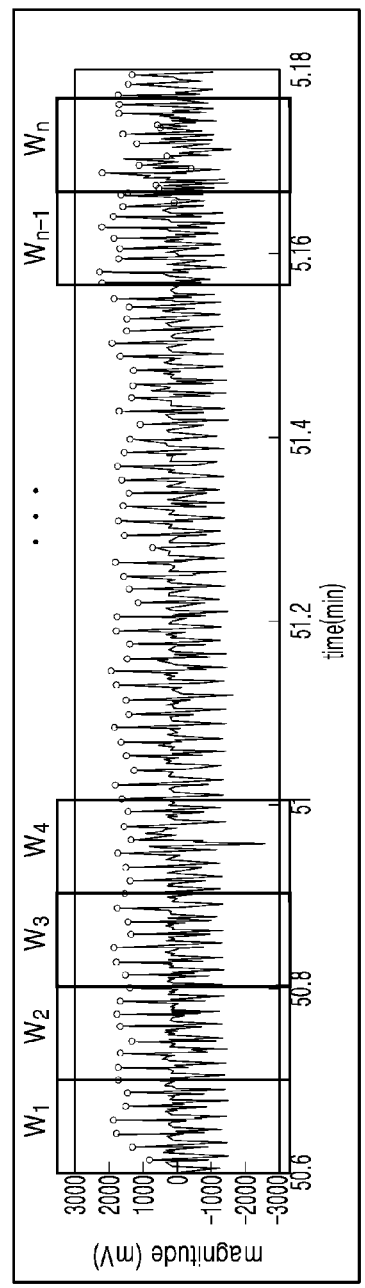
FIG. 4A is an exemplary diagram of windows of an electrocardiogram signal according to embodiments of the present disclosure.
Figure 4B:
FIG. 4B is an exemplary diagram of a window including an abnormal peak extracted according to embodiments of the present disclosure.
Figure 4C:
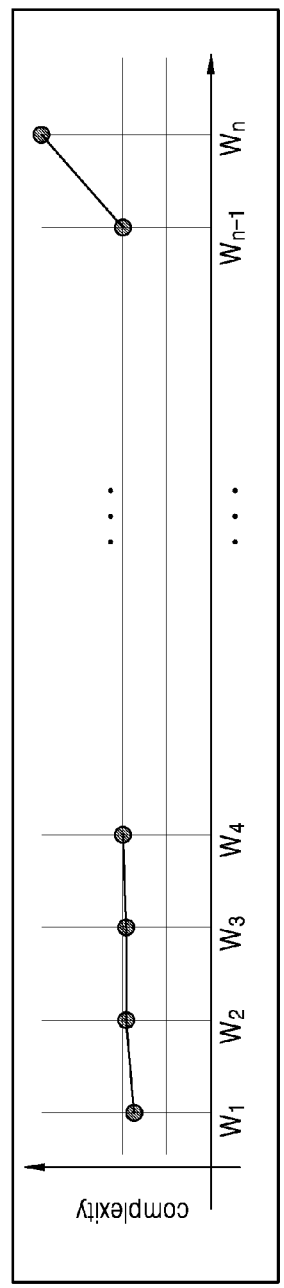
FIG. 4C is an exemplary diagram of complexity values calculated for windows of an electrocardiogram signal.

FIG. 4A, FIG. 4B and FIG. 4C are plots illustrating a process of determining whether or not there is abnormality by using the complexity of an electrocardiogram signal. FIG. 4A is an exemplary diagram of windows of an electrocardiogram signal according to embodiments of the present disclosure. FIG. 4B is an exemplary diagram of a window including an abnormal peak extracted according to embodiments of the present disclosure. FIG. 4C is an exemplary diagram of complexity values calculated for windows of an electrocardiogram signal.

As illustrated in FIG. 4A, in the first determination step S120, the complexity to which windows $W_1$, $W_2$, $W_3$, $W_4$, $W_{n-1}$, and $W_n$ of a preset size (time interval) are applied is calculated for the electrocardiogram signal. As illustrated in FIG. 3B, the electrocardiogram signal of a window out of a preset range is determined as an abnormal electrocardiogram signal. The abnormal electrocardiogram signal Wn may include one or more intervals and waveforms. As illustrated in FIG. 3C, for each widow $W_1$, $W_2$, $W_3$, $W_4$, $W_{n-1}$, and $W_n$, the complexity can be calculated.

A method of calculating the complexity of a signal may include, for example, Shannon entropy, turning point ratio (TPR), and root mean square of the successive difference (RMSSD). Various known techniques may be used as the method of calculating the complexity of a signal, and thus, separate description will not be made.

Figure 5A:
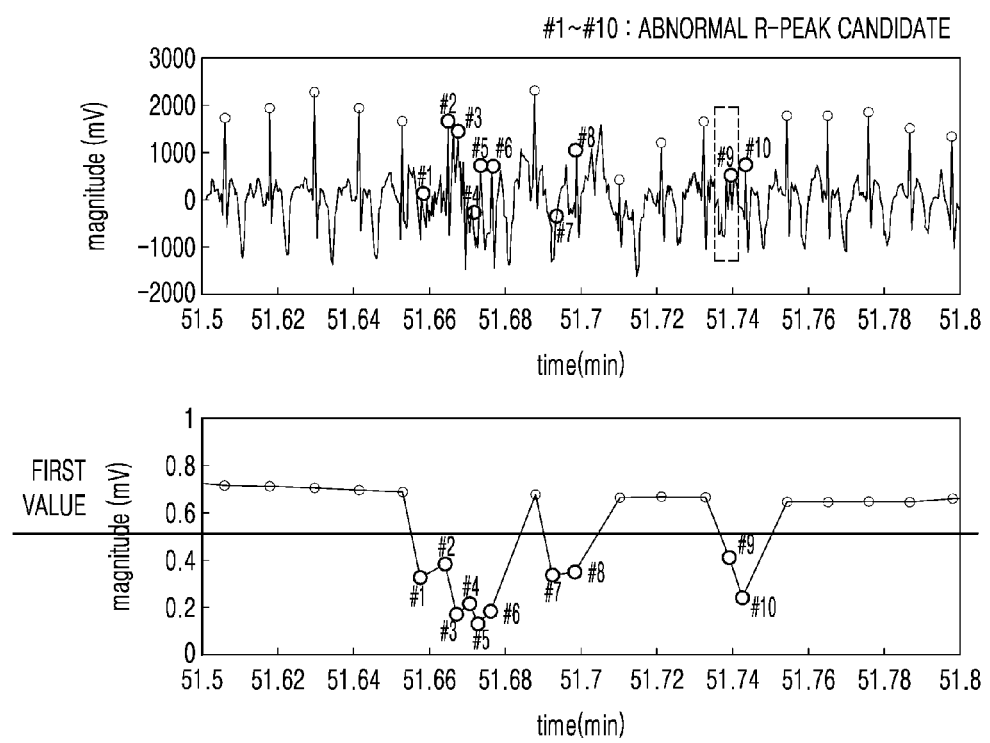
FIG. 5A is an exemplary diagram of R-peaks of an electrocardiogram signal generated according to embodiments of the present disclosure.
Figure 5B:
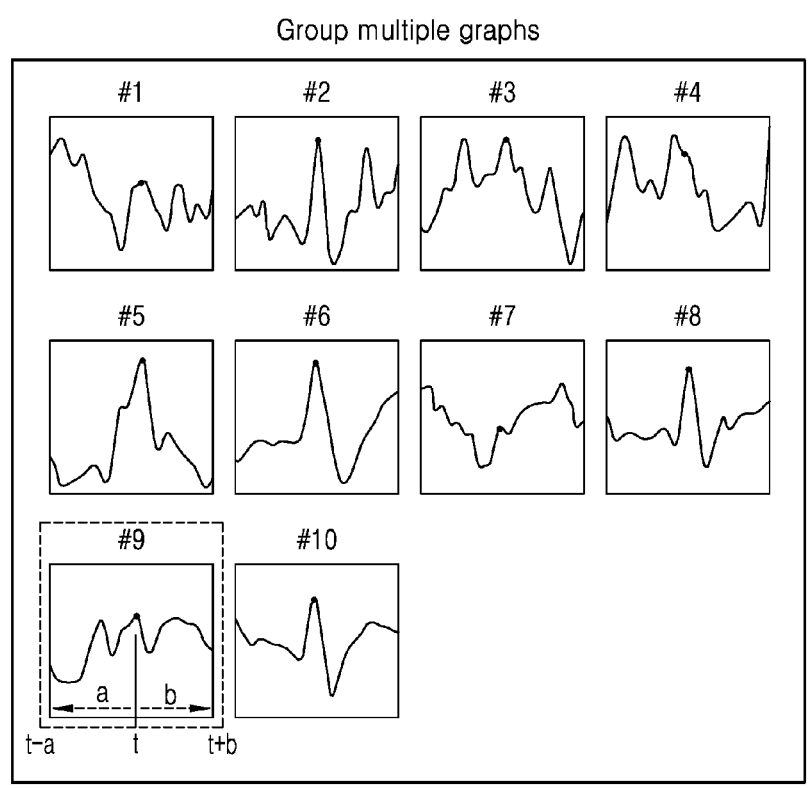
FIG. 5B is an exemplary diagram of signal waveforms of sections selected from an electrocardiogram signal.
Figure 6A:
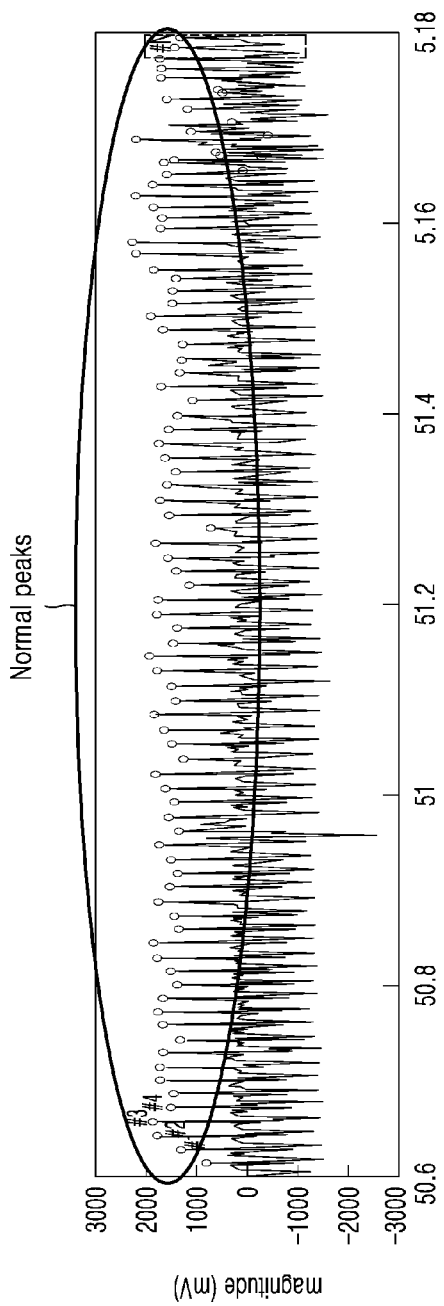
FIG. 6A is an exemplary diagram of normal peaks extracted from an electrocardiogram signal.
Figure 6B:
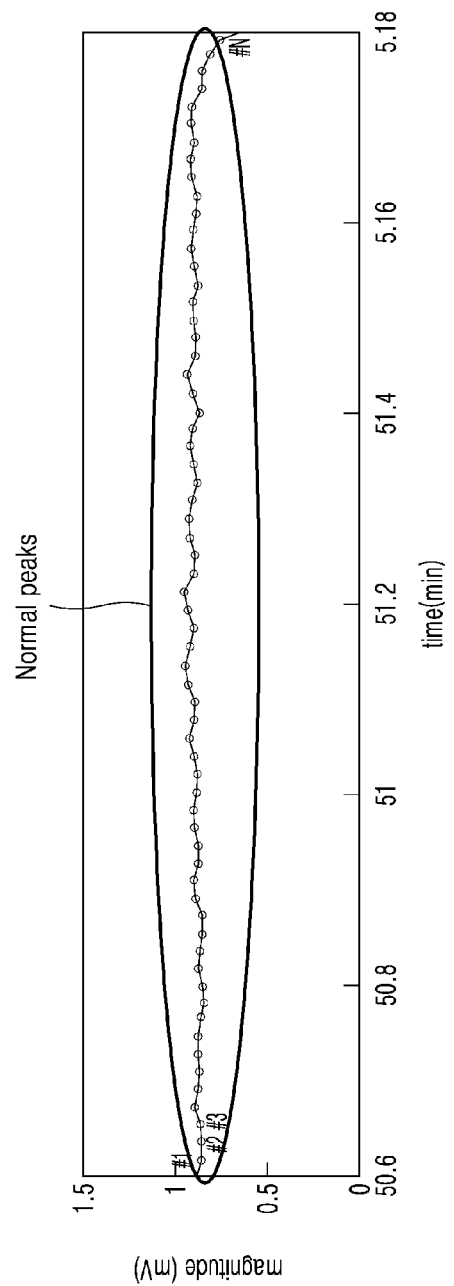
FIG. 6B is an exemplary diagram of peak interval values of normal peaks.
Figure 6C:
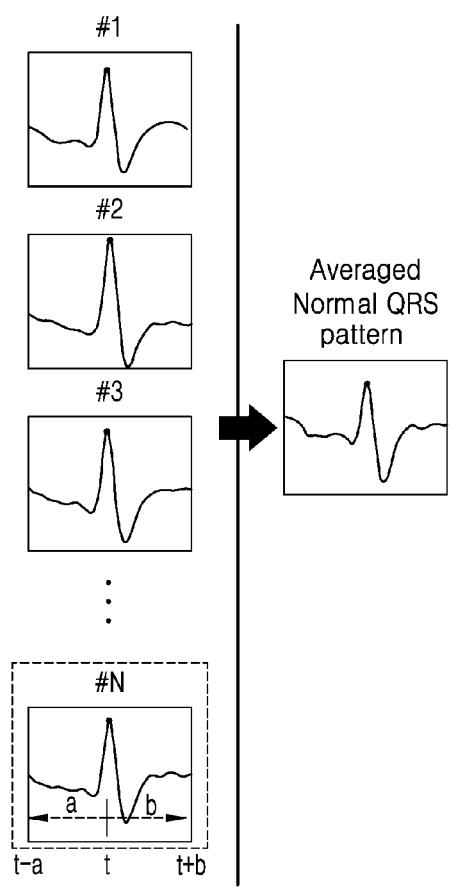
FIG. 6C is an exemplary diagram of signal waveforms for each section.

FIG. 5A and FIG. 5B are explanatory plots of waveforms of an abnormal electrocardiogram signal selected in the first determination step S120. FIG. 6A, FIG. 6B, and FIG. 6C are explanatory diagrams illustrating a method of calculating an average value of waveforms of an electrocardiogram signal, and FIG. 7A and FIG. 7B are explanatory plots of a determination result of the second determination step S130.

FIG. 5A is an exemplary diagram of R-peaks of an electrocardiogram signal generated according to embodiments of the present disclosure. FIG. 5B is an exemplary diagram of signal waveforms of sections selected from an electrocardiogram signal.

FIG. 6A is an exemplary diagram of normal peaks extracted from an electrocardiogram signal. FIG. 6B is an exemplary diagram of peak interval values of normal peaks; FIG. 6C is an exemplary diagram of signal waveforms for each section.

Figure 7A:
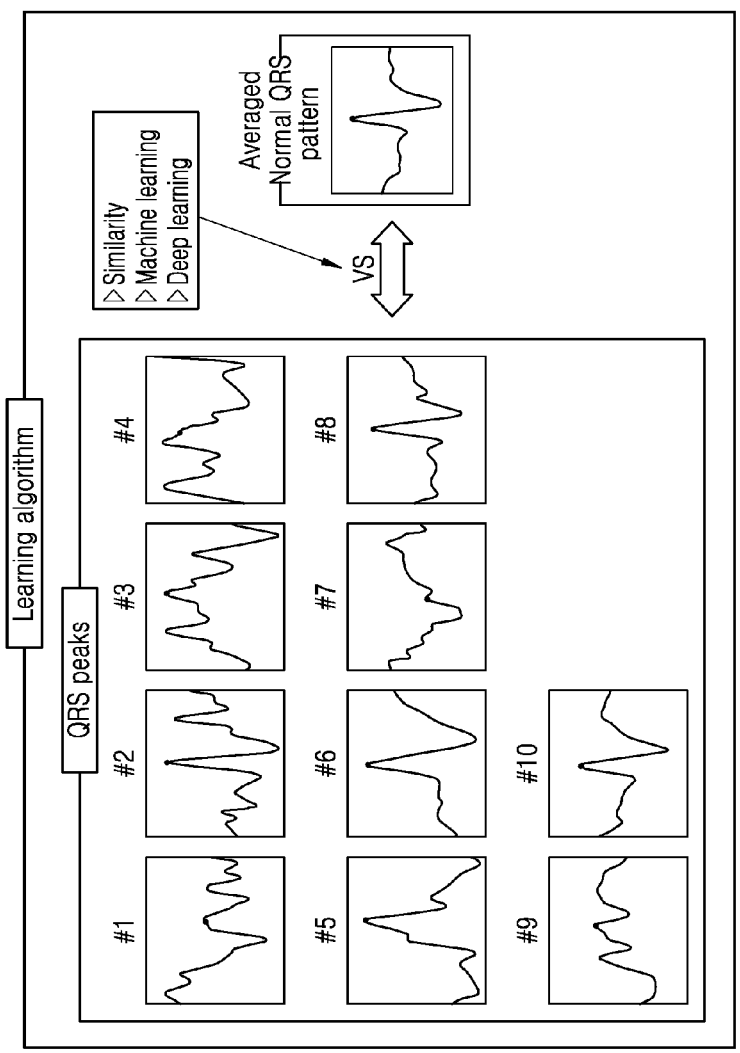
FIG. 7A is an exemplary diagram of signal waveforms for each section and an average normal QRS pattern extracted from signal waveforms.
Figure 7B:
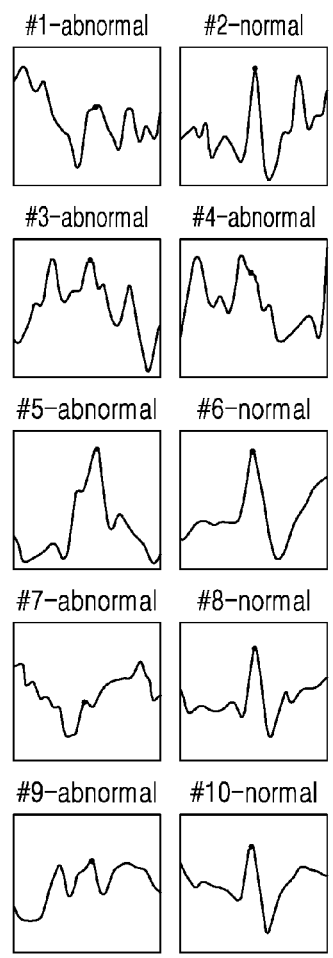
FIG. 7B is an exemplary diagram of whether each signal waveform is abnormal using an Average Normal QRS pattern.

FIG. 7A is an exemplary diagram of signal waveforms for each section and an average normal QRS pattern extracted from signal waveforms. FIG. 7B is an exemplary diagram of whether each signal waveform is abnormal using an Average Normal QRS pattern.

The second determination step S130 will be described in detail with reference to FIGS. 5A to 7B.

In the second determination step S130, the electrocardiogram signal processing device may compare a waveform of the selected abnormal electrocardiogram signal with a waveform of a normal electrocardiogram signal as illustrated in FIG. 5C. As illustrated in FIG. 5B, whether or not the electrocardiogram signal is abnormal is secondarily determined by comparing a waveform of the selected abnormal electrocardiogram signal with a waveform of a normal electrocardiogram signal by using an electrocardiogram signal processing device in the first determination step S120.

As illustrated in FIG. 6A, the electrocardiogram signal processing device may extract peaks from the electrocardiogram signal.

As illustrated in FIG. 6B, the waveform of the normal electrocardiogram signal is determined based on an average value of time intervals of waveforms of the electrocardiogram signal during a preset time period, in the second determination step S130. That is, a waveform of an electrocardiogram signal having N R-peaks may be included in the preset time period. As illustrated in FIG. 6C, the waveform of the electrocardiogram signal may include one pattern including a period from time t-a to time t+b, which is a preset region having a measurement time (or generation time) t of each R-peak as the center. The electrocardiogram signal processing device calculates an average value of time intervals between N waveforms of an electrocardiogram signal and desirably uses the average value of the time intervals of one or more waveforms of the electrocardiogram signal as a waveform of a normal electrocardiogram signal in the second determination step S130.

Specifically, in the second determination step S130, the electrocardiogram signal processing device compares each pattern with the waveform of the normal electrocardiogram signal by using the period from the time t-a to the time t+b, which is a preset region having a measurement time (or generation time) t of an R-peak of an abnormal electrocardiogram signal as the center in the first determination step S120.

The electrocardiogram signal processing device may also use artificial intelligence such as machine learning or deep learning or may also use a similarity determination method using feature points as a comparison method that may be used in the second determination step S130.

In the first determination step and the second determination step, whether or not an electrocardiogram signal is abnormal may be determined by using different criteria.

In the second determination step, the electrocardiogram signal processing device may determine whether or not the electrocardiogram signal is abnormal except for the abnormal period determined in the first determination step.

As can be seen from FIG. 7A, among ten abnormal electrocardiogram signals determined to be abnormal in the first determination step S110, the second electrocardiogram signal, the sixth electrocardiogram signal, the eighth electrocardiogram signal, and the tenth electrocardiogram signal are determined as normal electrocardiogram signals in the second determination step S130. As can be seen from FIG. 7B, the first electrocardiogram signal, the third electrocardiogram signal, the fourth electrocardiogram signal, the fifth electrocardiogram signal, the seventh electrocardiogram signal, and the ninth electrocardiogram signal are finally determined as abnormal electrocardiogram signals in the second determination step S130.

FIG. 8A, FIG. 8B, FIG. 8C and FIG. 8D illustrate explanatory diagrams of the confirmation step S140.

Figure 8A:
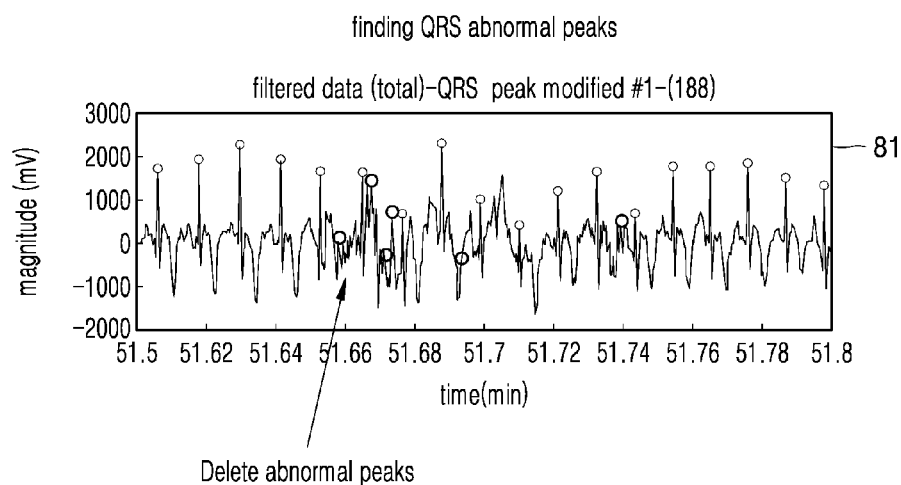
FIG. 8A is a diagram illustrating a process of deleting abnormal peaks from an electrocardiogram signal.
Figure 8B:
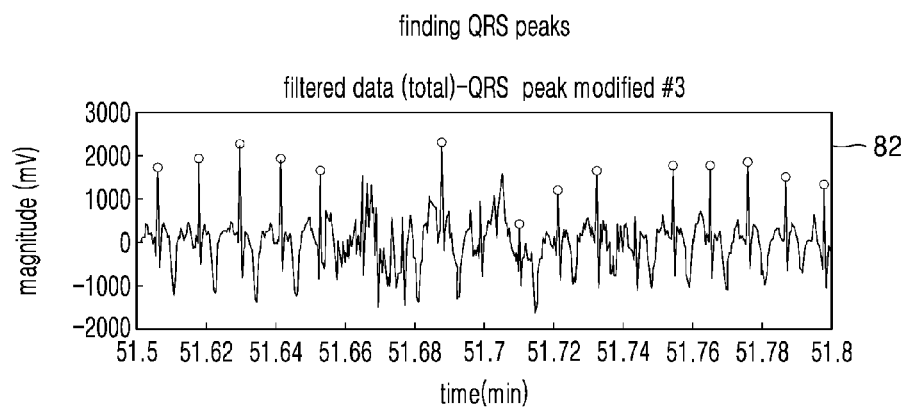
FIG. 8B is a diagram illustrating a process of deleting abnormal peaks from an electrocardiogram signal.
Figure 8C:
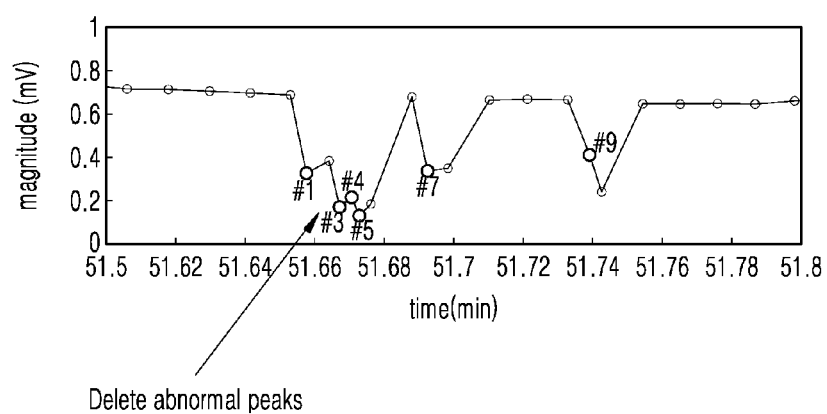
FIG. 8C is an exemplary diagram of peak values extracted from the electrocardiogram signal.
Figure 8D:
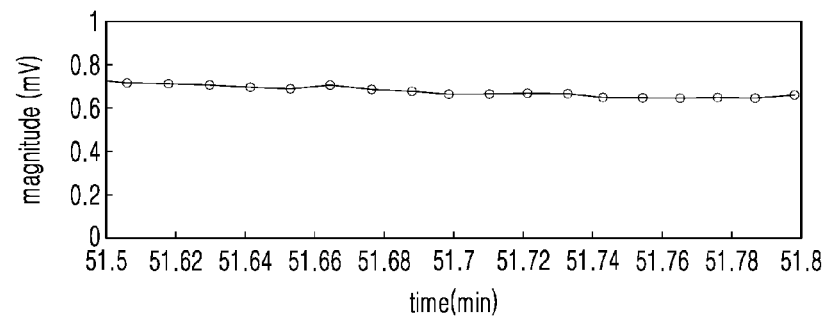
FIG. 8D is an exemplary diagram of peak values excluding abnormal peaks from the ECG signal.

FIG. 8A is an exemplary diagram of extracting R-peaks from the electrocardiogram signal 81, and FIG. 8C is an exemplary diagram of peak values of the electrocardiogram signal 81. FIG. 8D is an exemplary diagram of peak values excluding abnormal peaks from the ECG signal 82.

As can be seen from FIG. 8B and FIG. 8D, in the confirmation step S140, the electrocardiogram signal processing device may determine normal R-peaks by excluding R-peaks of the electrocardiogram signal determined to be abnormal in the second determination step S130.

Figure 9:
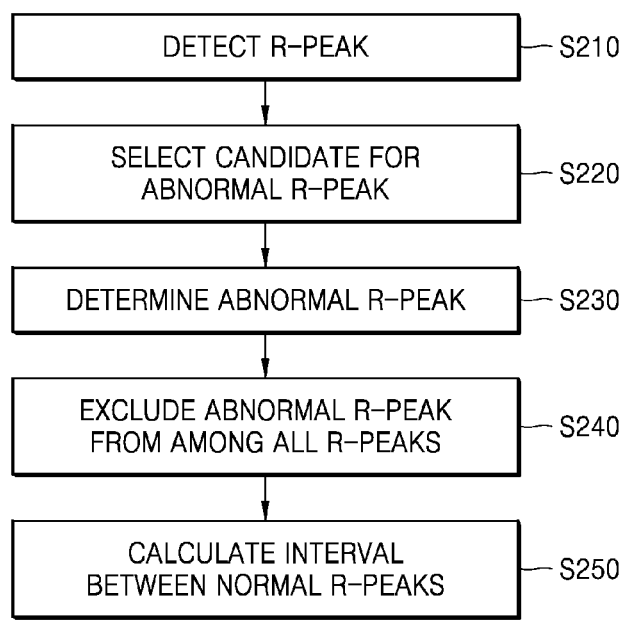
FIG. 9 is a flowchart when viewing, from another viewpoint, the flowchart of the method of processing an electrocardiogram signal according to the embodiment of the present disclosure illustrated in FIG. 1.

FIG. 9 is a flowchart when viewing, from another viewpoint, the flowchart of the method of processing an electrocardiogram signal according to the embodiment of the present disclosure illustrated in FIG. 1.

As can be seen from FIG. 9, the method of processing an electrocardiogram signal, according to the embodiment of the present disclosure, includes an R-peak detection step S210 of detecting an R-peak of an electrocardiogram signal by using an electrocardiogram signal processing device; a step S220 of selecting candidates for an abnormal R-peak from the electrocardiogram signal by using the electrocardiogram signal processing device; a step S230 of determining an abnormal R-peak among the candidates selected by the electrocardiogram signal processing device in step S220; a step S240 of excluding the abnormal R-peak determined in step S230 among all of the R-peaks from the electrocardiogram signal; and a step of calculating an interval between normal R-peaks confirmed by the electrocardiogram signal processing device in step S240.

In step S220, at least one of a time interval between R-peaks of an electrocardiogram signal, and complexity of the electrocardiogram signal may be used.

Specifically, when using the time interval between the R-peaks of the electrocardiogram signal, step S220 includes step S221a of calculating an interval between the R-peaks of the electrocardiogram signal; and step S333a of selecting the corresponding R-peak as a candidate for an abnormal R-peak when the interval between the R-peaks calculated in step S221a is less than a preset value.

In addition, when using the complexity of the electrocardiogram signal, step S220 desirably includes step S221b of calculating the complexity of a signal to a preset window size; and step S222b of selecting an R-peak included in a window in which the complexity of the signal calculated in step S221b is out of a preset range, as a candidate for an abnormal R-peak.

In addition, in step S230, an abnormal R-peak is determined from among the candidates selected in step S220 by comparing a waveform of an electrocardiogram signal during a time period previously set based on the time representing the R-peak selected in step S220 with a waveform of an electrocardiogram signal representing a normal R-peak.

In addition, the waveform of the electrocardiogram signal representing the normal R-peak may be calculated by an average value of time intervals of waveforms of the electrocardiogram signal for multiple R-peaks during a preset time period.

As described above, according to the method of processing an electrocardiogram signal, according to the present disclosure, an electrocardiogram signal processing device detects a candidate for an abnormal electrocardiogram signal in step 1, and the abnormal electrocardiogram signal may be finally and accurately determined in step 2. In addition, when an abnormal electrocardiogram signal is determined in step 2 without being processed as in step 1, the amount of calculations is increased, and determination of the abnormal electrocardiogram signal due to a small amount of calculations may be made by adding step 1

That is, according to the method of processing an electrocardiogram signal, according to the present disclosure, it can be seen that an abnormal electrocardiogram signal may be accurately determined by determining whether or not an electrocardiogram signal is abnormal through the two steps.

The device described above may be implemented with hardware components, software components, and/or a combination of hardware components and software components. For example, the device and components described in the embodiments may be implemented with one or more general purpose computers or special purpose computers, such as a processor, a controller, an arithmetic logic unit (ALU), a digital signal processor, a microcomputer, a field programmable gate array (FPGA), a programmable logic unit (PLU), a microprocessor, or any other device capable of executing and responding to instructions. A processing device may execute an operating system (OS) and one or more software applications executed on the operating system. In addition, the processing device may also access, store, operate, process, and generate data in response to execution of software. For the sake of convenient understanding, one processing device may be used, but those skilled in the art will understand that the processing device may include a plurality of processing elements and/or multiple types of processing elements. For example, the processing device may include a plurality of processors or one processor and one controller. In addition, other processing configurations such as a parallel processor are possible.

The software may include a computer program, code, instructions, or a combination thereof, may operate the processing device as desired, or may independently or collectively instruct the processing device. Software and/or data may be interpreted by a processing device or may be permanently or temporarily embodied for any type of machine, component, physical device, virtual equipment, computer storage medium or device, or signal wave being transmitted to provide instructions or data to a processing device. Software may also be distributed to computer systems connected to each other via a network to be stored or executed in a distributed manner. Software and data may be stored in one or more computer-readable recording media.

According to the method of processing an electrocardiogram signal, according to the present disclosure, an abnormal electrocardiogram signal may be accurately determined by determining whether or not the electrocardiogram signal is abnormal through two steps.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A method of processing an electrocardiogram signal by an electrocardiogram signal processing device including at least one processor, the method comprising:
    calculating one or more time intervals between peaks of an electrocardiogram signal;
    determining peaks having time interval less than a preset first value as a first abnormal period of the electrocardiogram signal; and
    determining whether or not the electrocardiogram signal without the first abnormal period is abnormal by comparing the electrocardiogram signal without the first abnormal period with a pattern of a preset region having a measurement time of an R peak of a normal electrocardiogram signal using a machine learning model,
    wherein the preset first value is set by using an average value of time intervals between normal R-peaks.

2. The method of claim 1, further comprising:
    selecting normal R-peaks of the electrocardiogram signal upon determination that the electrocardiogram signal is normal.

3. The method of claim 2, further comprising, after the normal R-peaks are selected, obtaining a heart rate or heart rate variability based on time intervals between the normal R-peaks.

4. The method of claim 2, further comprising, after the normal R-peaks are selected, storing signal periods including the normal R-peaks in a memory or transmitted to an external device.

5. The method of claim 1, wherein the step of determining of whether or not the electrocardiogram signal is abnormal further includes determining a period of an abnormal electrocardiogram signal included in a window,
    during the period, a complexity of the electrocardiogram signal, calculated for a window of a preset size, being out of a preset range such that the period is determined as an abnormal electrocardiogram signal period.

6. The method according to claim 5, wherein
    the machine learning model is generated based on waveforms of periods except for the first abnormal period of the electrocardiogram signal, and
    the machine learning model is by using waveforms of the first abnormal period in the electrocardiogram signal.

7. The method according to claim 1, wherein the step of determining of whether or not the electrocardiogram signal without the first abnormal period is abnormal further includes:
    determining whether or not the electrocardiogram signal is abnormal by using the machine learning model generated based on waveforms of periods except for a previously obtained abnormal period of the electrocardiogram signal, and
    updating the machine learning model by using waveforms of the first abnormal period in the electrocardiogram signal.

8. The method according to claim 7, wherein the step of determining whether or not the electrocardiogram signal without the first abnormal period is abnormal further comprises determining whether or not the electrocardiogram signal is abnormal by using the machine-learning based on waveforms of the electrocardiogram signal acquired from a plurality of objects.

9. The method according to claim 1, wherein the step of determining whether or not the electrocardiogram signal without the first abnormal period is abnormal further comprises determining whether or not the electrocardiogram signal is abnormal by using the machine-learning algorithm based on waveforms of the electrocardiogram signal acquired from a plurality of objects.

* * * * *